(12) United States Patent
Yu et al.

(10) Patent No.: US 8,314,266 B2
(45) Date of Patent: Nov. 20, 2012

(54) METHOD FOR MANUFACTURING ESTERS FROM ACID AND ALCOHOL AND SYSTEM THEREOF

(75) Inventors: Cheng-Ching Yu, Taipei (TW); Hsiao-Ping Huang, Taipei (TW); Ming-Jer Lee, Taipei (TW); Ruei-Chiang Tsai, Taipei (TW); Jian-Kai Cheng, Taipei (TW)

(73) Assignees: China Petrochemical Development Corporation, Taipei (TW); National Taiwan University, Taipei (TW)

( * ) Notice: Subject to any disclaimer, the term of this patent is extended or adjusted under 35 U.S.C. 154(b) by 659 days.

(21) Appl. No.: 12/220,940

(22) Filed: Jul. 30, 2008

(65) Prior Publication Data
US 2009/0198083 A1   Aug. 6, 2009

(30) Foreign Application Priority Data

Jan. 31, 2008   (TW) ............................... 97103641 A

(51) Int. Cl.
*C07C 67/08*   (2006.01)
(52) U.S. Cl. ...................................................... 560/265
(58) Field of Classification Search .................. None
See application file for complete search history.

(56) References Cited

U.S. PATENT DOCUMENTS

2006/0178524 A1*   8/2006   Zuber et al. .................. 560/231

\* cited by examiner

*Primary Examiner* — Paul A Zucker
(74) *Attorney, Agent, or Firm* — Edwards Wildman Palmer LLP; Peter F. Corless

(57) ABSTRACT

A process for manufacturing esters from acid and alcohol and a system thereof are provided, wherein the system includes a reactive distillation column, a sidestream reactor packed with catalyst, and a decanter for conducting the method. The method is carried out by (a) extracting a first mixture of acid and alcohol from the reactive distillation column, for then feeding the first mixture to at least one sidestream reactor packed with catalyst to obtain a reaction product; (b) feeding the reaction product from the sidestream reactor to the reactive distillation column, allowing a second mixture of alcohol, ester and water to be separated from a top end of the reactive distillation column; (c) feeding the second mixture into the decanter to separate an organic phase from an aqueous phase; and (d) separating esters from the organic phase. The method and system allow the esters to be extracted without using a plurality of recovering columns and decanters, and are capable of improving packing/changing catalyst in a single reactive distillation column.

19 Claims, 6 Drawing Sheets

METHOD FOR MANUFACTURING ESTERS FROM ACID AND ALCOHOL AND SYSTEM THEREOF

BACKGROUND OF THE INVENTION

1. Field of the Invention

The present invention relates to methods for manufacturing esters from acid and alcohol, and more particularly, to a method for manufacturing esters from acid and alcohol in a reactive distillation column and a system for carrying out the method.

2. Description of Related Art

Ethyl acetate, isopropyl acetate, and butyl acetate are important solvents in the industry for manufacturing plastic, grease, printing ink and so on. They can also be used for preparing synthetic flavor materials. There are a number of literatures related to methods for manufacturing ethyl acetates, which may be divided into the following categories in general:

(i) A pre-reactor is used for esterifying acetic acide to obtain ester products. The ester products are extracted and purified by a plurality of recovering columns and decanters. However, such a method is complicated to operate and costly to maintain as it involves a higher quantity of equipments and devices.

(ii) A reactive distillation column is used, which is primarily divided into a reaction section, a rectification section and a stripping section. Homogenous and heterogeneous catalysts are used to speed up the reaction.

(iii) A reactive distillation columns and a recovering column are used to obtain highly purified ethyl acetate from the bottom of the recovering column. However, the mixture of acid, alcohol and ester at the top of the recovering column has to be sent back to the reactive distillation column, and the aqueous alcohol solution at the bottom of the reactive distillation column has to be also processed.

Among the above conventional methods, the second one that a single reactive distillation column is used is most preferred, such that there are many discussions on literatures thereof. However, data disclosed by these literatures reveal that the method using a single reactive distillation column does not produce ethyl acetate with desired purity, making it fail to meet the industrial requirement. It is because the acid, alcohol and ester from an azeotropic mixture at the top of the reactive distillation column and the boiling point of the acetic acid at the bottom of the reactive distillation column is relatively high, making undesired products thus-obtained have to be reprocessed or eliminated.

In view of the above drawbacks, Taiwanese Patent No. TWI282746 discloses an improved system using a single reactive distillation column. The system is primarily made up of a reaction distillation column, a liquid decanter, and an ester recovering column, allowing the reactants to be fed into the reactive distillation column via the bottom plate thereof. The reactive distillation column is divided into a rectification section and a reactive section which is primarily filled with a solid catalyst and positioned between the upper portion and the bottom plate or between the middle portion and the bottom plate of the reactive distillation column. The liquid decanter then separates the azeotrope of alcohol-ester-water entered from the top plate of the reactive distillation column. Subsequently, a portion of the organic phase thus-separated is returned to the top plate of the reactive distillation column, while the rest of the organic phase is fed to the ester recovering column for extracting an ester product of a high purity, which can be obtained at the bottom of the ester recovering column.

However, problems in operation and design still exist in these reactive distillation mechanisms. In particular, in terms of filling the reactive distillation column with heterogeneous catalysts, there are often problems such as catalyst deterioration, and hardware design difficult for filling and refilling. Hence it is still required to have a method for making esters of a high purity above the industrial level as well as overcoming the drawback of the single reactive distillation column.

SUMMARY OF THE INVENTION

In order to achieve the above and other objectives, the present invention provides a method for manufacturing esters from acid and alcohol, which includes the steps of: feeding into a sidestream reactor packed with catalysts a first mixture having acid and alcohol from a reactive distillation column, in order to obtain a reaction product; feeding the reaction product from the sidestream reactor to the reactive distillation column so as to separate a second mixture having alcohol, ester and water from a top end of the reactive distillation column; feeding the second mixture to a decanter for separating the second mixture into an organic phase and an aqueous phase; and separating esters meeting an industrial level from the organic phase.

The present invention also provides a system for manufacturing esters from acid and alcohol, including: (a) a reactive distillation column for receiving feedings of acid and alcohol to form a first mixture, and allowing a second mixture having alcohol, ester, and water to be formed at a top end of the reactive distillation column; (b) a sidestream reactor with a catalyst packed therein and for receiving the first mixture from the reactive distillation column, so as to subject the first mixture to an esterification reaction, to obtain a reaction product which is then fed back to the reactive distillation column; and (c) a decanter for receiving the second mixture from the top end of the reactive distillation column, so as to separate the second mixture into an phase rich in esters and an aqueous phase.

A process for manufacturing esters from acid and alcohol and a system thereof are provided, wherein the system includes a reactive distillation column, a sidestream reactor packed with catalyst, and a decanter for conducting the method. The method is carried out by (a) extracting a first mixture of acid and alcohol from the reactive distillation column, for then feeding the first mixture to at least one sidestream reactor packed with catalyst to obtain a reaction product; (b) feeding the reaction product from the sidestream reactor to the reactive distillation column, allowing a second mixture of alcohol, ester and water to be separated from a top end of the reactive distillation column; (c) feeding the second mixture into the decanter to separate an organic phase from an aqueous phase; and (d) separating esters from the organic phase. The method and system allow the esters to be extracted without using a plurality of recovering columns and decanters, and are capable of improving packing/changing catalyst in a single reactive distillation column.

DETAILED DESCRIPTION OF PREFERRED EMBODIMENTS

Preferred embodiments of a multi-substrate region-based package and a method for fabricating the same proposed by the present invention are described in detail as follows with reference to FIGS. 1 to 6.

The method of the present invention primarily focuses on an esterification reaction between acid and alcohol as reactants to form esters. The esterification reaction is described by the following formula:

 acid+alcohol    ester+water

The reaction is a reversible reaction, wherein an example of an acid is acetic acid, examples of an alcohol include ethanol, isopropanol and butanol, and examples of an ester include ethyl acetate, isopropyl acetate or butyl acetate. Homogeneous catalysts and heterogeneous catalysts are two major catalysts required for the reaction. In the method of the present invention, a heterogeneous solid catalyst is used. The advantage of the catalyst is that it can be disposed on the desired locations (such as bottom plate, sidestream reactor, bottom plate and reactor or pre-reactor) by employing a packing method, and thus the place for the reaction can be flexibly selected without causing problems related to recovery of liquid catalysts. The solid catalyst may be an ion exchange resin which is frequently used in the industry, such as amberlyst 15 (Rohm and Hass) or purolite CT179 (Purolite) and so on. The catalyst packing structure can adopt the well-known Katapak-S method or use a fixture device positioned in a column plate (Davy Process Technology).

In a method according to a first embodiment of the present invention, acetic acid and ethanol are used as reactants to produce ethyl acetate. In the reaction system, the boiling point of acetic acid is 118.01° C., indicating a heavy component. The boiling point of the azeotropic mixture of alcohol, ester and water is 70.09° C., indicating a light component. The boiling point, 77.20° C., of the product, ethyl acetate, lies at the mid-boiling point. The boiling point of each of the components in the reaction system is listed in Table 1.

TABLE 1

| Type of Substance | Boiling Point | Azeotropic Composition (mole %) |
|---|---|---|
| Ethanol/Ethyl Acetate/Water | 70.09 | Ethanol = 11.26<br>Ethly Acetate = 57.89<br>Water = 68.85 |
| Ethyl Acetate/Water | 70.37 | Ethyl Acetate = 68.85<br>Water = 31.15 |
| Ethanol/Ethyl Acetate | 71.81 | Ethanol = 46.20<br>Ethyl Acetate = 53.80 |
| Ethyl Acetate | 77.20 | — |
| Ethanol/Water | 78.18 | Ethanol = 90.37<br>Water = 9.63 |
| Ethanol | 78.31 | — |
| Water | 100.0 | — |
| Acetic Acid | 118.01 | — |

Figure 1:
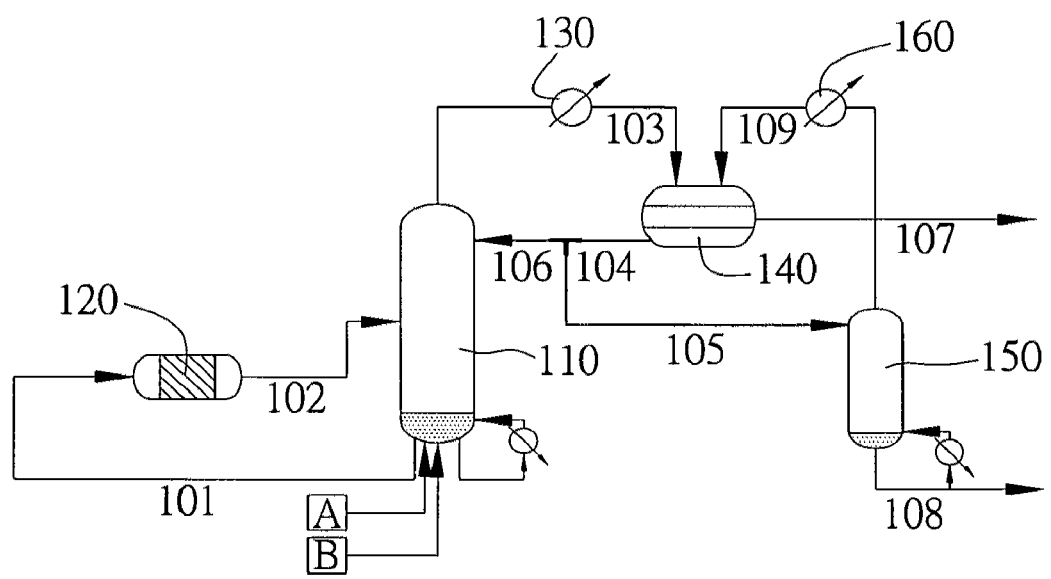
FIG. 1 is a schematic diagram illustrating a method according to a first embodiment of the present invention.

As shown in FIG. 1, according to the first embodiment of the present invention, acetic acid and ethanol are directly and continuously fed, in a molar ratio of 0.94:1 to 0.96:1, to the bottom end of the reactive distillation column 110, or fed to an inlet first (not shown) and subsequently fed to the bottom end of the reactive distillation column 110 in the form of an azeotropic composition, in order to obtain highly purified ethyl acetate. The total number of the plates in the reactive distillation column 110 is 20, including a reactive column plate and a stripping column plate. The temperature of the reactive distillation column 110 is between 70 and 125° C., and preferably between 75 and 123° C. A large amount of acid will remain in the bottom end of the reactive distillation column 110, thereby making the bottom end contain a high concentration of reactants, and thus the bottom end of the reactive distillation column 110 can be regarded as requiring packed solid catalysts. On the other hand, the bottom end of the reactive distillation column 110 contains a high concentration of reactants and has a higher temperature, a liquid mixture including acid and alcohol is extracted from the bottom end and fed to a sidestream reactor 120 packed with a catalyst via a pipe 101 for performing an esterification reaction. The reaction temperature of the sidestream reactor 120 depends on the temperatures of the extracted substances, and does not need to be additionally set.

The reaction quantity of the sidestream reactor 120 can be changed by adjusting the amount of the catalyst at the bottom plate of the reactive distillation column 110. For example, the reaction quantity of the sidestream reactor 120 is about 8 to 15%, and preferably 11%, of the total reaction quantity, so as to lower the total annual cost of the reaction. Besides, the bottom plate of the reactive distillation column is not filled with catalysts, and instead, only a single sidestream reactor for reaction is used to increase the flow of the extracted substances to meet the required specification. On the other hand, adjusting the reaction product of the sidestream reactor 120 and recycling the product to the position of the reactive distillation column 110, such as recycling the product to the middle portion of the eighth to tenth plate, and preferably to the ninth plate, in the reactive distillation column 110 via a pipe 102, are advantageous to lowering the total annual cost.

A first mixture of alcohol, ester, and water formed at the top end of the reactive distillation column is fed to a decanter via a pipe 103. In the embodiment, a gaseous mixture comprising alcohol, ester and water is extracted from the top end of the reactive distillation column 110, condensed to liquid in a condenser 130, and then fed to a liquid decanter 140, for separating into an organic phase rich in esters and an aqueous phase. The temperature of the decanter is between the room temperature and 50° C., and preferably at 40° C. In the embodiment, after the organic phase rich in esters is outputted from the liquid decanter 140 via a pipe 104, a portion of the organic solvent is fed to the ester recovering column 150 via a pipe 105 to extract esters with a purity reaching an industrial level, and the other portion is recycled to the reactive distillation column 110 via a pipe 106 to recover the organic phase. The aqueous phase is then guided out of the decanter 140 via a pipe 107. After investigation, it is found that the flow rate of the extracted substances fed to the sidestream reactor 120 from the reactive distillation column 110 is 3 to 4 times, and preferably approximately 3.7 times, higher than the recovery rate of organic solvent, to achieves lower total annual cost.

The organic phase separated in decanter 140, after being fed to the ester recovering column 150 via a pipe 105, can be used for extracting highly purified esters with purity above the industrial level in the bottom end, and then the esters are outputted from the ester recovering column 150 via a pipe 108. The stripped gaseous mixture in the top end of the ester recovering column 150 is condensed to liquid in a condenser 160, and is then fed to the liquid decanter 140 via a pipe 109, for another phase separation. The ester recovering column 150 is between 70 and 95° C., and preferably between 75 and 85° C.

Figure 2:
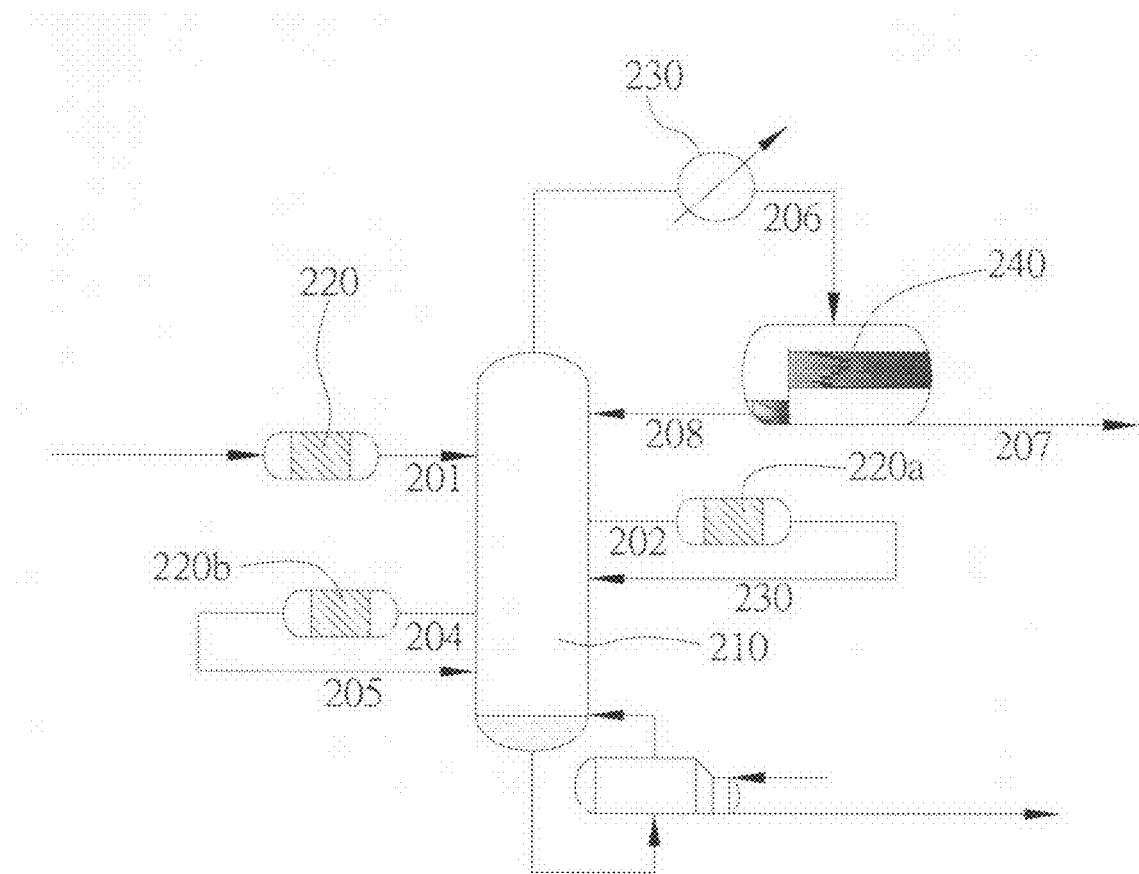
FIG. 2 is a schematic diagram illustrating a method according to a second embodiment of the present invention.

FIG. 2 illustrates the second embodiment of the present invention. In the embodiment, ethanol and butanol are used as reactants to produce butyl ethanoate. In the reaction system, the boiling point of butyl ethanoate is 126.01° C. indicating a heavy component. The boiling point of the azeotropic mixture of alcohol, ester and water is 90.68° C. indicating a light component. The boiling point of each of the components in the reaction system is listed in Table 2:

TABLE 2

| Type of Substance | Boiling Point | Azeotropic Composition (mole %) |
|---|---|---|
| n-Butanol/Butyl Ethanoate/Water | 90.68 | n-Butanol = 20.6<br>Butyl Ethanoate = 70.76<br>Water = 8.64 |
| Butyl Ethanoate/Water | 90.96 | Butyl Ethanoate = 28.23<br>Water = 71.77 |
| n-Butanol/Water | 90.62 | n-Butanol = 24.51<br>Water = 75.49 |
| Water | 100 | — |
| n-Butanol/Butyl Ethanoate | 116.85 | n-Butanol = 78.47<br>Butyl Ethanoate = 21.53 |
| n-Butanol | 117.68 | — |
| Acetic Acid | 118.01 | — |
| Butyl Ethanoate | 126.01 | — |

In the embodiment, the total number of plates in the distillation column 210 is 29. Acetic acid and n-butanol are fed into a pre-reactor 220 and subsequently fed to the top end of the distillation column 210 via a pipe 201, between the 21st and the 23rd plate, preferably at the 22nd plate, of the distillation column 210, so as to achieve the goal of lowering total annual cost. Besides the pre-reactor 220, the distillation column 210 must be equipped with two sidestream reactors 220a and 220b packed with catalysts to form a system with a 1PR+2SR structure.

By adjusting the extraction rate of the mixture fed to the sidestream reactor from the distillation column 210 where the mixture is extracted, and the location where each of the reactors extracts substances from the distillation column 210 and the location where the substances are recycled to the plate of the distillation column, the goal of lowering the total annual cost can be achieved. In a preferred embodiment, the location where the reaction products of the sidestream reactors 220a and 220b are returned to the distillation column 210 is positioned in the bottom end of the location where the liquid mixture is extracted. For example, the first sidestream reactor 220a extracts the liquid mixture containing acid and alcohol from the 20th plate in the distillation column 210 via a pipe 202, for esterification. The reaction product is then recycled to the position of the 18th plate in the distillation column 210 via a pipe 203. The second side reactor 220b extracts the liquid mixture containing acid and alcohol from the 14th plate in the distillation column 210 via a pipe 204, for esterification, and the reaction product is then returned to the 11th plate in the distillation column 210 via a pipe 205.

A gaseous mixture is formed at the upper portion of the distillation column 210, condensed to liquid in a condenser 230, and then fed to a liquid decanter 240 via a pipe 206 for separation into an organic phase and an aqueous phase. The aqueous phase separated in the decanter 240 is guided out of the decanter 240 via a pipe 207. The organic solvent is then recycled to the distillation column 210 via a pipe 208, and esters are extracted from the bottom end of the distillation column.

Figure 3:
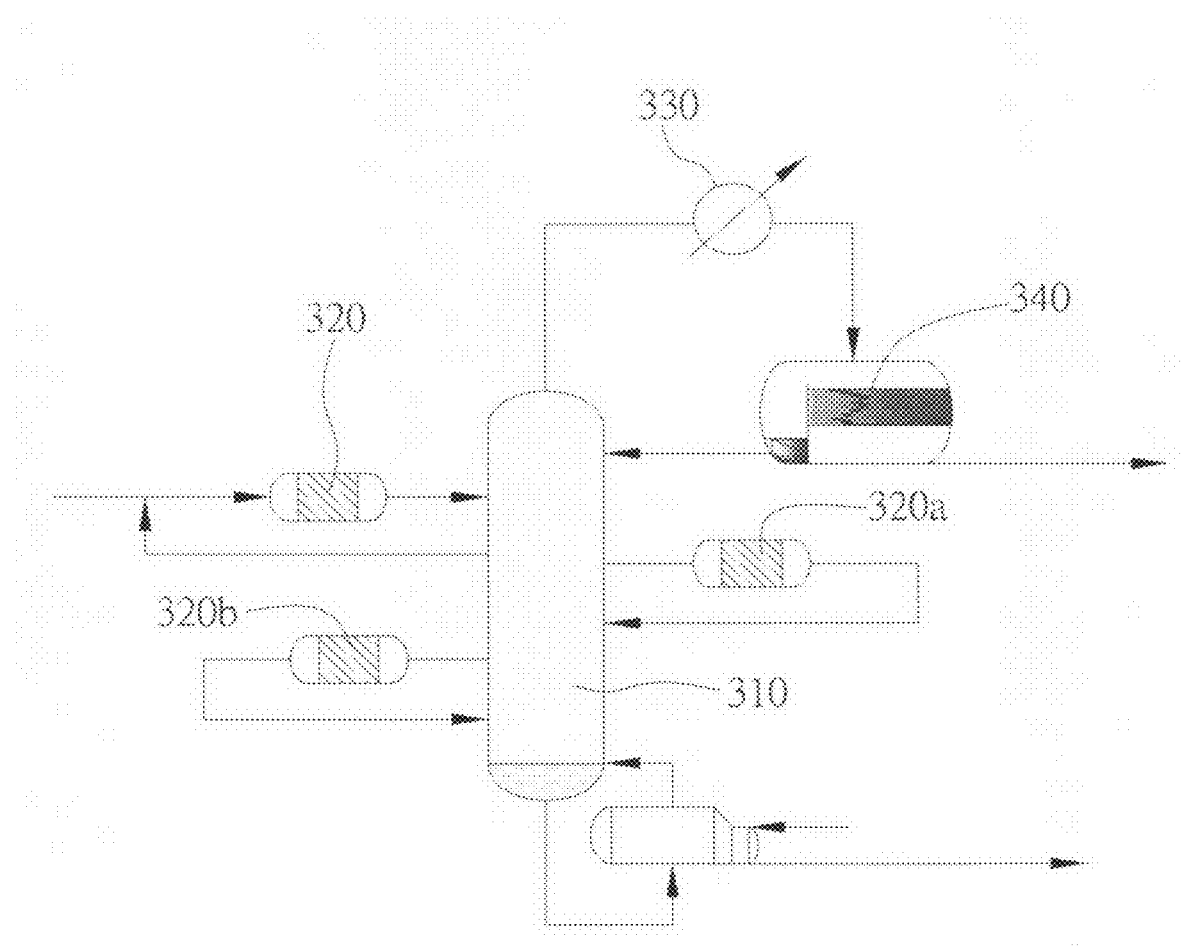
FIG. 3 is a schematic diagram illustrating a method according to a third embodiment of the present invention.

FIG. 3 illustrates the method according to a third embodiment of the present invention. Similar to the second embodiment, butyl acetate is produced from acetic acid and butanol. In the embodiment, the mixture extracted from the distillation column 310 is re-fed to the pre-reactor 320, thereby allowing the pre-reactor 320 to act as the sidestream reactor at the same time. In addition, the distillation column 210 must be equipped with two sidestream reactors 220a and 220b packed with catalysts to form a system with a 3SR structure.

By adjusting the extraction rate of the mixture fed to the sidestream reactor from the distillation column 310 where the mixture is extracted, and the location where the reactors 320 extract substances from the distillation column 310 and the location where the substances are recycled to the plate of the distillation column, the goal of lowering the total annual cost can be achieved. In a preferred embodiment, the sidestream reactor 320 extracts the liquid mixture containing acid and alcohol from the 23th plate in the distillation column 310 via a pipe, for esterification, and the product is recycled to the $24^{th}$ plate in the distillation column 310.

A gaseous mixture is formed at the upper portion of the distillation column 310, condensed to liquid in a condenser 330, and then fed to a liquid decanter 340 via a pipe for separation into an organic phase and an aqueous phase. The aqueous phase separated in the decanter 340 is guided out of the decanter 340 via a pipe, whereas the organic solvent is then recycled to the distillation column 210, and esters are extracted from the bottom end of the distillation column.

Figure 4:
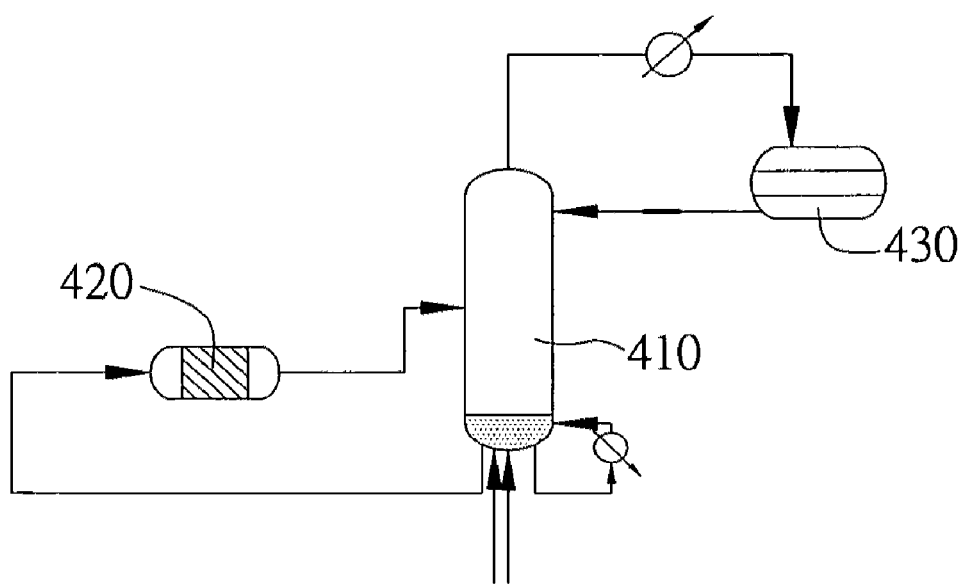
FIG. 4 is a schematic diagram illustrating a system according to a first embodiment of the present invention.

As shown in FIG. 4, a first embodiment of the system for making esters from acid and alcohol in the present invention is shown. The system includes a reactive distillation column 410 for receiving feedings of acid and alcohol and forming a first mixture having alcohol, ester and water in the top end of the column, a sidestream reactor 420 packed with catalysts, for receiving a liquid mixture extracted from the reactive distillation column, for esterification, the product is recycled to the reactive distillation column, wherein the mixture contains acid and alcohol; and a decanter 430 for receiving a first mixture extracted from the top end of the reactive distillation column, and separating the first mixture into an organic phase rich in esters and an aqueous phase.

Figure 5:
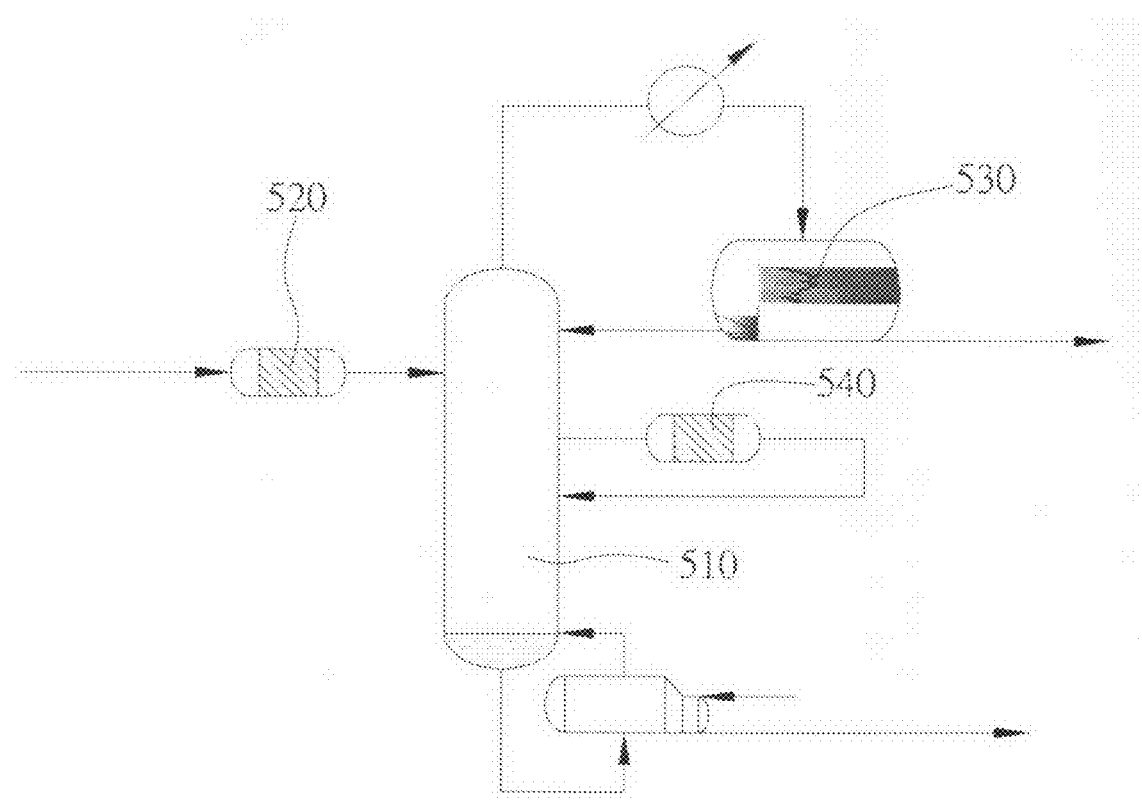
FIG. 5 is a schematic diagram illustrating a system according to a second embodiment of the present invention.

FIG. 5 shows a system for making esters from acid and alcohol according to a second embodiment of the present invention. In the present embodiment, the system includes a reactive distillation column 510 for receiving feedings of acid and alcohol and forming a first mixture having alcohol, ester and water in the top end of the column, a sidestream reactor 540 for receiving a liquid mixture containing acid and alcohol and is extracted from the reactive distillation column, for esterification, the product is recycled to the reactive distillation column; and a decanter 530 for receiving a first mixture extracted from the top end of the reactive distillation column, and separating the first mixture into an organic phase rich in esters and an aqueous phase. On the other hand, the system further comprises a pre-reactor 520 for reacting acid with alcohol prior to feeding to the distillation column.

Figure 6:
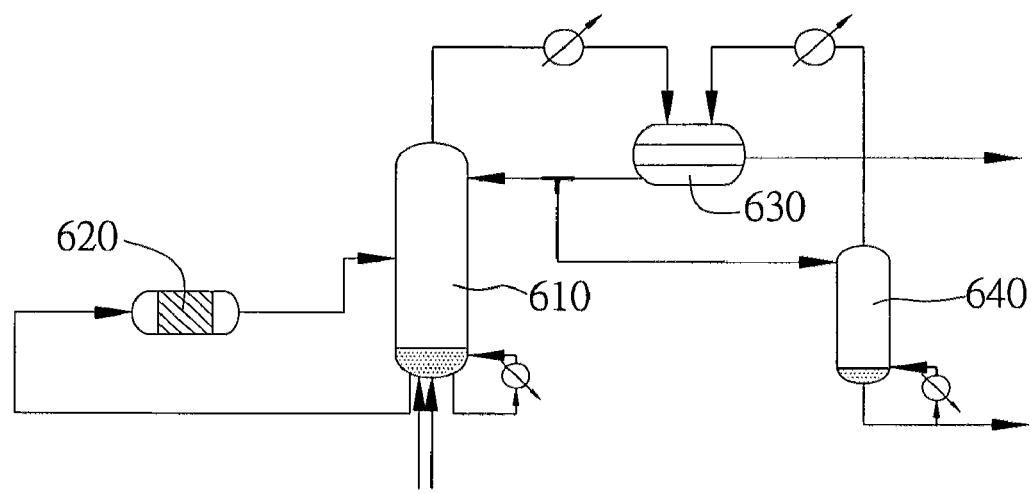
FIG. 6 is a schematic diagram illustrating a system according to a third embodiment of the present invention.

FIG. 6 shows a system for making esters using acid and alcohol according to a third embodiment of the present invention. In the present embodiment, the system includes a reactive distillation column 610 for receiving feedings of acid and alcohol and forming a first mixture having alcohol, ester and water in the top end of the column, a sidestream reactor 620 for receiving a liquid mixture containing acid and alcohol and is extracted from the reactive distillation column, for esterification, the product is recycled to the reactive distillation column; and a decanter 630 for receiving a first mixture extracted from the top end of the reactive distillation column, and separating the first mixture into an organic phase rich in esters and an aqueous phase. On the other hand, the system further comprises an ester recovering column 640 for separating an organic phase with purity higher than an industrial level.

EXAMPLE 1

According to the method in a first embodiment of the present invention, acetic acid and ethanol were used as reactants. The reactants were fed into the reactive distillation column in a molar ratio of 0.9652. The operating temperature of the reactive distillation column was between 75 and 123° C. The operating temperature of the reboiler is 70° C. Amberlyst 35 catalyst was used to pack the coupled sidestream reactor (the lower portion of the distillation column was not packed with catalysts). The operating temperature of the liquid decanter was 40° C. The operating temperature of the ester recovering column was between 75 and 85° C. The operating temperature of the reboiler was 70° C. Ethyl acetate with a concentration of 0.99 was obtained as a reaction product. Results are shown in table 3.

EXAMPLE 2

According to the method in a first embodiment of the present invention, acetic acid and ethanol were used as reactants. The reactants were fed into the reactive distillation column in a molar ratio of 0.9652. The operating temperature of the reactive distillation column was between 75 and 123° C. The operating temperature of the reboiler is 70° C. Amberlyst 35 catalyst was used to pack the coupled sidestream reactor and the lower portion of the distillation column. The operating temperature of the liquid decanter was 40° C. The operating temperature of the ester recovering column was between 75 and 85° C. The operating temperature of the reboiler was 70° C. Ethyl acetate with a concentration of 0.99 was obtained as a reaction product. Results are shown in table 3.

TABLE 3

| | System | | | |
|---|---|---|---|---|
| | First Embodiment | | Second Embodiment | |
| Item | Distillation Column | Ester Recovering Column | Distillation Column | Ester Recovering Column |
| General Theoretical Plate | 20 | 10 | 20 | 10 |
| Catalyst-packed in the bottom end of the Column | No | | Yes | |
| Position of the Column Plate For Extraction of Sidestream | Bottom Plate | | Bottom Plate | |
| Position of the Column Plate For Recycling Sidestream | 10 | | 10 | |
| Ratio of Sidestream/ Return Flow | | | | |
| Acetic Acid Feeding Plate | Sidestream Reactor | | Bottom Plate | |
| Ethanol Feeding Plate | Sidestream Reactor | | Bottom Plate | |
| Acetic Acid Feeding Concentration (Molar Ratio) | 0.95 | | 0.95 | |
| Ethanol Feeding Concentration (Molar Ratio) | 0.87 | | 0.87 | |
| Acetic Acid/Ethanol Stoichiometric Ratio | 0.9652 | | 0.9652 | |
| Ester Concentration of (Mole Ratio) | | 0.99000 | | 0.99000 |
| Liquid Decanter (° C.) | 40 | | 40 | |

EXAMPLE 3

The first embodiment was repeated. Acetic acid and isopropanol were used as reactants to obtain isopropyl acetate with a concentration of 0.99 obtained as a reaction product.

EXAMPLE 4

The second embodiment was repeated. Acetic acid and isopropanol were used as reactants to obtain isopropyl acetate with a concentration of 0.99 obtained as a reaction product.

According to the experimental results, the method of the present invention is capable of effectively separating out esters with purity meeting an industrial level, without the need of applying multiple recovering columns and decanter. In comparison with the single reactive distillation column system without the use of sidearm reactors, the method and the system of the present invention are able to resolve problems such as packaging/changing the catalysts of the reactive distillation column. Moreover, the methods and systems of the present invention, when applied to the continuous industrial production, have the advantage of lowering the total annual total cost.

The present invention has been described using exemplary preferred embodiments. However, it is to be understood that the scope of the present invention is not limited to the disclosed arrangements. The scope of the claims, therefore, should be accorded the broadest interpretation, so as to encompass all such modifications and similar arrangements.

What is claimed is:

1. A method for manufacturing ester from acid and alcohol, comprising the steps of:
   (a) extracting a first mixture having acid and alcohol from a reactive distillation column and feeding the first mixture into at least a sidestream reactor packed with a catalyst in order to obtain a reaction product;
   (b) feeding the reaction product from the sidestream reactor to the reactive distillation column so as to separate a second mixture having alcohol, ester and water from the top end of the reactive distillation column;
   (c) feeding the second mixture to a decanter to separate an organic phase from an aqueous solvent; and
   (d) separating the ester from the organic phase, wherein the bottom end of the reactive distillation column is free from being packed with the catalyst, and the flow rate of the first mixture extracted from the reactive distillation column and fed to the sidestream reactor is 3 to 4 times higher than the recovery rate of the organic phase recycled to the reactive distillation column.

2. The method of claim 1, wherein the acid is acetic acid.

3. The method of claim 1, wherein the alcohol is selected from a group consisting of ethanol, isopropanol, and butanol.

4. The method of claim 1, wherein the reactive distillation column comprises a reactive column plate and a stripping column plate.

5. The method of claim 1, wherein the reactive distillation column is between 70 and 125° C. in temperature.

6. The method of claim 1, wherein the temperature of the decanter is between room temperature and 50° C.

7. The method of claim 1, wherein the acid and alcohol are continuously fed into the reactive distillation column in a molar ratio ranging from 0.94:1 to 0.96:1.

8. The method of claim 1, wherein the acid and alcohol are continuously fed into the reactive distillation column in a form of azeotrope.

9. The method of claim 1, wherein the first mixture is extracted from the bottom end of the reactive distillation column.

10. The method of claim 1, wherein the reaction product from the sidestream reactor is fed to a middle portion of the reactive distillation column.

11. The method of claim 1, wherein the reaction quantity in the sidestream reactor accounts for 8-15% of the total reaction quantity.

12. The method of claim 1, wherein the acid and alcohol are independently and continuously fed into the reactive distillation column.

13. The method of claim 1, wherein the acid and alcohol are fed into a pre-reactor and then continuously introduced into the top end of the reactive distillation column from the pre-reactor.

14. The method of claim 1, wherein the position of the reactive distillation column where the reaction product from the sidestream reactor is fed is predelimitationined to locate below the top end of the reactive distillation column from where the first mixture is extracted.

15. The method of claim 1, wherein the step (c) further comprises:
feeding back a first portion of the organic phase to the reactive distillation column; and
feeding a second portion of the organic phase into an ester recovering column.

16. The method of claim 1, wherein the step (d) further comprises:
feeding the organic phase into an ester recovering column for separating the ester from a gaseous mixture; and
feeding the gaseous mixture into the decanter.

17. The method of claim 16, wherein the ester recovering column is between 70 and 95° C. in temperature.

18. The method of claim 1, wherein the step (c) further comprises feeding back the organic phase to the reactive distillation column.

19. The method of claim 1, wherein the step (d) further comprises extracting the ester from the bottom end of the distillation column.

* * * * *